US008011830B2

(12) United States Patent
Schueler et al.

(10) Patent No.: US 8,011,830 B2
(45) Date of Patent: Sep. 6, 2011

(54) METHOD AND SYSTEM FOR CALIBRATING AN X-RAY PHOTOELECTRON SPECTROSCOPY MEASUREMENT

(75) Inventors: Bruno W. Schueler, San Jose, CA (US); David A. Reed, Belmont, CA (US); Bruce H. Newcome, Sunnyvale, CA (US); Jeffrey A. Moore, San Jose, CA (US)

(73) Assignee: Revera Incorporated, Santa Clara, CA (US)

( * ) Notice: Subject to any disclaimer, the term of this patent is extended or adjusted under 35 U.S.C. 154(b) by 206 days.

(21) Appl. No.: 12/430,687

(22) Filed: Apr. 27, 2009

(65) Prior Publication Data

US 2009/0268877 A1    Oct. 29, 2009

Related U.S. Application Data

(60) Provisional application No. 61/048,811, filed on Apr. 29, 2008.

(51) Int. Cl.
*G01D 18/00* (2006.01)

(52) U.S. Cl. .......................................... 378/207; 378/84

(58) Field of Classification Search .................... 378/84, 378/85, 207; 250/305
See application file for complete search history.

(56) References Cited

U.S. PATENT DOCUMENTS

| | | | |
|---|---|---|---|
| 5,028,778 A * | 7/1991 | Ninomiya et al. | 250/305 |
| 5,148,462 A * | 9/1992 | Spitsyn et al. | 378/143 |
| 5,245,648 A * | 9/1993 | Kinney et al. | 378/85 |
| 5,635,709 A * | 6/1997 | Sliski et al. | 378/207 |
| 6,596,994 B1 * | 7/2003 | Alkire et al. | 378/205 |
| 6,717,162 B1 * | 4/2004 | Jongen | 250/505.1 |
| 2004/0264641 A1 * | 12/2004 | Chung | 378/84 |
| 2008/0219409 A1 * | 9/2008 | Ueda | 378/89 |

OTHER PUBLICATIONS

Cavalleri et al., "High resolution X-ray photoelectron spectroscopy of L-cysteine self-assembled films", Physical Chemistry Chemical Physics, (2004), vol. 6, pp. 4042-4046.*

Floreano et al., "Performance of the grating-crystal monochromator of the ALOISA beamline at the Elettra Synchrotron", Review of Scientific Instruments, (1999), vol. 70, Issue 10, pp. 3855-3864.*

* cited by examiner

*Primary Examiner* — Chih-Cheng G Kao
(74) *Attorney, Agent, or Firm* — Blakely, Sokoloff, Taylor & Zafman LLP

(57) ABSTRACT

A method and a system for calibrating an X-ray photoelectron spectroscopy (XPS) measurement are described. The method includes using an X-ray beam to generate an XPS signal from a sample and normalizing the XPS signal with a measured or estimated flux of the X-ray beam. The system includes an X-ray source for generating an X-ray beam and a sample holder for positioning a sample in a pathway of the X-ray beam. A detector is included for collecting an XPS signal generated by bombarding the sample with the X-ray beam. Also included are a flux detector for determining a measured or estimated flux of the X-ray beam and a computing system for normalizing the XPS signal with the measured or estimated flux of the X-ray beam.

26 Claims, 7 Drawing Sheets

METHOD AND SYSTEM FOR CALIBRATING AN X-RAY PHOTOELECTRON SPECTROSCOPY MEASUREMENT

This application claims the benefit of U.S. Provisional application Ser. No. 61/048,811, filed Apr. 29, 2008, entitled METHOD AND SYSTEM FOR CALIBRATING AN X-RAY PHOTOELECTRON SPECTROSCOPY MEASUREMENT

BACKGROUND OF THE INVENTION

1) Field of the Invention

The invention is in the field of X-ray Photoelectron Spectroscopy Analysis.

2) Description of Related Art

X-ray Photoelectron Spectroscopy (XPS) metrology commonly employs monochromatic aluminum Kα (AlKα) X-rays, which may be generated by bombarding an aluminum anode surface with a focused electron beam. A fraction of the generated AlKα X-rays is then intercepted by a focusing monochromator and a narrow X-ray energy band is focused onto the analysis site on a sample surface. The X-ray flux of the AlKα X-rays at the sample surface depends on the electron beam current, the thickness and integrity of the aluminum anode surface, and the stability of the monochromator. In general, the X-ray flux at the analysis site cannot easily be predicted with sub-percent precision. This may render calculations that include a value for X-ray flux insufficient in cases where the metrology requirements can be, e.g., 0.5% or less in error.

Typically, calculations using XPS measurements factor out the contribution of X-ray flux by using a ratio of two distinct XPS signals. For example, two different film thickness measurements may be used in a ratio, cancelling the X-ray flux value, in order to calculate the thickness of one of the two films. In such a calculation, one film is used as a known standard in analyzing the properties of the other film. However, it is not always the case that a sample readily includes a known standard quantity to which an unknown quantity may be calibrated. Furthermore, an XPS signal of a known standard quantity may have to be collected at a different time than the XPS signal for the unknown quantity. In that case, even though the contribution of X-ray flux is factored out of the calculation, the approach does not account for any changes in X-ray flux at the different times of collection of the XPS signals.

Thus, a method and a system for calibrating an XPS measurement are described herein.

DETAILED DESCRIPTION

Figure 1:
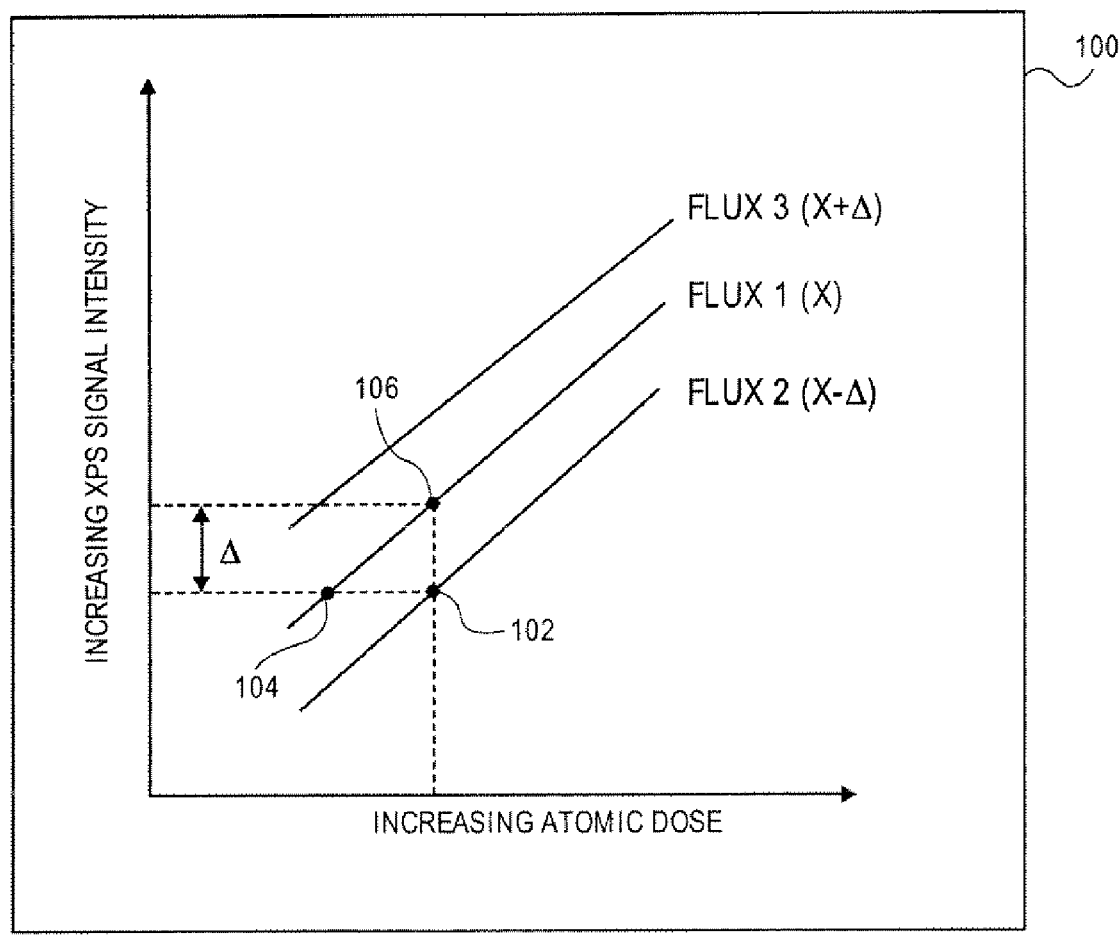
FIG. 1 is a plot of Increasing Signal Intensity versus Increasing Atomic Dose for three different X-ray flux values, in accordance with an embodiment of the present invention.

A method and a system for calibrating an X-ray photoelectron spectroscopy measurement are described. In the following description, numerous specific details are set forth, such as normalization techniques and system arrangements, in order to provide a thorough understanding of the present invention. It will be apparent to one skilled in the art that the present invention may be practiced without these specific details. In other instances, well-known features such as semiconductor stacks are not described in detail in order to not unnecessarily obscure the present invention. Furthermore, it is to be understood that the various embodiments shown in the Figures are illustrative representations and are not necessarily drawn to scale.

Disclosed herein are a method and a system for calibrating an X-ray photoelectron spectroscopy (XPS) measurement. The method may include using an X-ray beam to generate an XPS signal from a sample. In one embodiment, the XPS signal is then normalized with a measured or estimated flux of the X-ray beam. The system may include an X-ray source for generating an X-ray beam and a sample holder for positioning a sample in a pathway of the X-ray beam. A detector may be included for collecting an XPS signal generated by bombarding the sample with the X-ray beam. In one embodiment, a flux detector for determining a measured or estimated flux of the X-ray beam and a computing system for normalizing the XPS signal with the measured or estimated flux of the X-ray beam are also included.

By normalizing an XPS signal with a measured or estimated flux of an X-ray beam, an accurate XPS signal intensity may be obtained directly without the need for comparison with a second reference XPS signal. For example, in accordance with an embodiment of the present invention, an XPS signal is obtained from a sample. The intensity of the XPS signal correlates with an atomic dose value for the sample. Also, the XPS signal is directly proportional to the actual flux of the X-ray beam used to generate the XPS signal. Therefore, any discrepancy between a system calibrated X-ray flux value and the actual flux value would otherwise lead to a loss of accuracy in the correlation. However, in one embodiment, by normalizing the XPS signal intensity with the measured or estimated flux value (as referenced against the calibrated X-ray flux value), a more accurate correlation of XPS signal intensity with atomic dose value is determined. In an embodiment, normalizing an XPS signal in this way eliminates the need for obtaining a second reference XPS signal from the sample. In a specific embodiment, by eliminating the need for obtaining a second reference XPS signal from a sample, the throughput of samples (i.e. the rate at which samples are measured) may be increased for an XPS system. For example, in a particular embodiment, an XPS signal for a dielectric layer such as but not limited to silicon dioxide, silicon oxynitride, aluminum oxide or hafnium oxide is calibrated without having to obtain or reference an XPS signal of, e.g., an underlying silicon substrate.

In an aspect of the present invention, an XPS signal may be normalized with a measured or estimated flux of an X-ray beam. FIG. 1 is a plot 100 of Increasing Signal Intensity versus Increasing Atomic Dose for three different X-ray flux values, in accordance with an embodiment of the present invention.

Referring to FIG. 1, a calibration line FLUX is determined for a range of XPS signals. Calibration line FLUX 1 may represent a plot of intensity of an XPS measurement as a function of known atomic doses for a particular species of atoms in a range of calibration samples. For example, in accordance with an embodiment of the present invention, calibration line FLUX 1 represents increasing XPS signal intensity values correlated with increasing known atomic dose values for the particular atomic species. In one embodiment, a value point 106 represents a specific XPS signal intensity value correlated with a specific known atomic dose value in a calibration sample. Thus, by collecting a range of XPS signal intensity values, the known atomic doses for a particular atomic species in a range of calibration samples can be correlated with the signal intensity values to provide calibration line FLUX 1.

Calibration line FLUX 1 represents the correlation at an X-ray flux value, X. However, since XPS signal intensity varies directly with X-ray flux value, such a correlation holds only for the given X-ray flux value, X. Thus, in accordance with an embodiment of the present invention, a correlated atomic dose value will differ for a given XPS signal intensity, depending on the actual X-ray flux value of the X-ray beam used to generate the XPS signal. For example, referring to FIG. 1, a measurement line FLUX 2 represents a plot of intensity of XPS measurements as a function of atomic dose at an X-ray flux value, X−Δ, i.e. at an X-ray flux value less than the X-ray flux value for calibration line FLUX 1. In another embodiment, a measurement line FLUX 3 represents a plot of intensity of XPS measurements as a function of atomic dose at an X-ray flux value, X+Δ, i.e. an X-ray flux value greater than the X-ray flux value for calibration line FLUX 1.

As described above, the intensity of an XPS signal is directly proportional to the actual X-ray flux value. By way of example, in one embodiment, a value point 102 represents a specific XPS signal intensity value correlated with a specific atomic dose value for measurement line FLUX 2. However, measurement line FLUX 2 represents the correlation at an X-ray flux value, x−Δ. Therefore, value point 102 is located at a lower XPS signal intensity value than is value point 106 for the same atomic dose value. Accordingly, there is a discrepancy in XPS signal intensity value for the same atomic dose value, as dependent upon the X-ray flux value. If one were to assume an X-ray flux value equal to the calibrated X-ray flux value, X, then an inaccurate value point 104 would mistakenly be correlated with a lower than actual atomic dose value (i.e. the value point is shifted left). Instead, in accordance with an embodiment of the present invention, by normalizing an XPS signal with a measured or estimated flux of an X-ray beam, an accurate XPS signal intensity correlated with atomic dose is obtained.

Normalization of a measured XPS signal intensity may be used to correct for a discrepancy in XPS signal intensity value as it varies with the actual X-ray flux value. In accordance with an embodiment of the present invention, an actual X-ray flux value of an X-ray beam used to generate an XPS signal is measured or estimated. The actual X-ray flux value is then compared with a calibration X-ray flux value. The calibrated X-ray flux value may be, e.g., the optimal or the statistically most occurring X-ray flux value for an X-ray beam typically generated in a particular XPS system. The intensity of the generated XPS signal is normalized according to equation (1) based on the discrepancy between the measured or estimated actual X-ray flux value and the calibration X-ray flux value, in order to provide a calibrated XPS signal intensity:

$$XPS_{calibrated} = XPS_{measured} \times (Flux_{calibrated}/Flux_{measured\ or\ estimated}) \quad (1)$$

where $XPS_{calibrated}$ is the normalized XPS signal intensity, $XPS_{measured}$ is the generated XPS signal intensity, $Flux_{calibrated}$ is the calibration X-ray flux value, and $Flux_{measured\ or\ estimated}$ an approximated of the actual X-ray flux value. Thus, normalizing the XPS signal intensity with a measured or estimated flux value includes referencing the measured or estimated flux value against a calibrated X-ray flux value. In accordance with an embodiment of the present invention, a more realistic correlation of atomic dose value with XPS signal intensity is obtained. In one embodiment, the determined atomic dose is used to calculate the thickness of a film in a sample. In another embodiment, the determined atomic dose is used to calculate the depth to which a particular atomic species is incorporated into a sample. In another embodiment, the determined atomic dose is used to calculate a concentration ratio of several atomic species in a sample.

Figure 2:
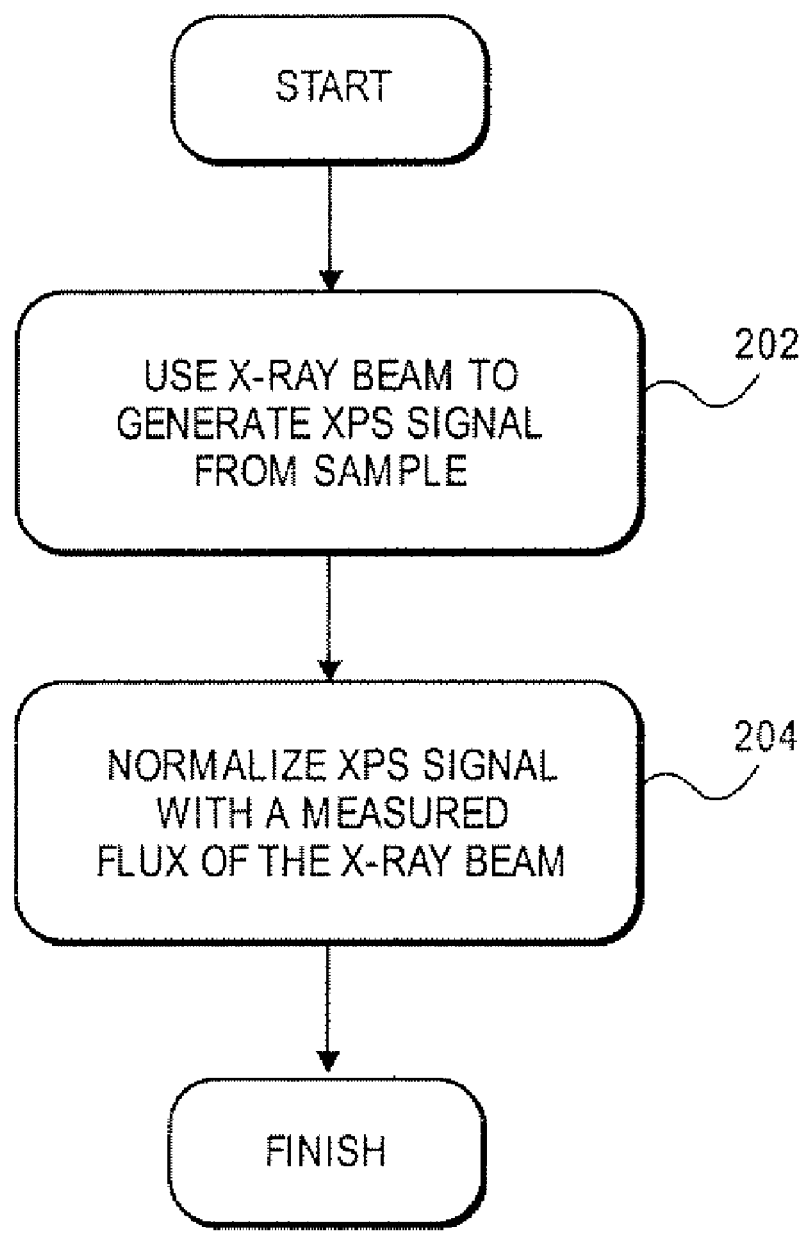
FIG. 2 is a Flowchart representing a series of operations in a method for calibrating an X-ray photoelectron spectroscopy measurement, in accordance with an embodiment of the present invention.

Thus, in an aspect of the present invention, an XPS signal may be calibrated. FIG. 2 is a Flowchart 200 representing a series of operations in a method for calibrating an XPS measurement, in accordance with an embodiment of the present invention.

Referring to operation 202 of Flowchart 200, an X-ray beam is used to generate an XPS signal obtained by bombarding a sample with the X-ray beam. In operation 204, the XPS signal is normalized with a measured or estimated flux of the X-ray beam. In accordance with an embodiment of the present invention, the XPS signal is normalized according to equation (1). In one embodiment, the measured or estimated flux of the X-ray beam is obtained prior to generating the XPS signal from the sample. In another embodiment, the measured or estimated flux of the X-ray beam is obtained subsequent to generating the XPS signal from the sample. In yet another embodiment, the measured or estimated flux of the X-ray beam is obtained at approximately the same time as generating the XPS signal from the sample. In an embodiment, the measured or estimated flux of the X-ray beam is time-integrated to provide a measurement representative of a duration approximately equal to the duration of a sample measurement.

Figure 3:
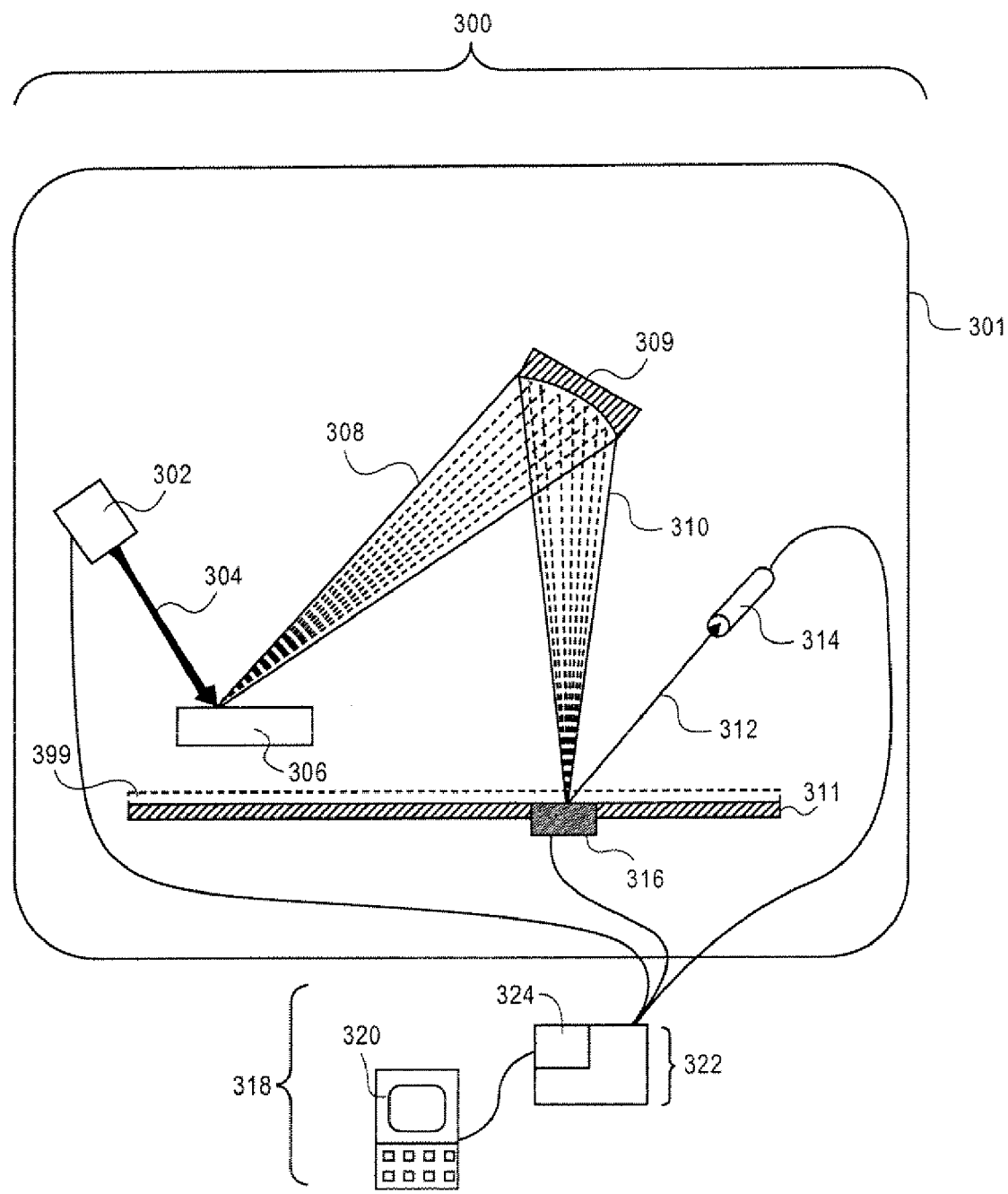
FIG. 3 is an illustration representing a system for obtaining and calibrating an X-ray photoelectron spectroscopy measurement and including a flux detector positioned at a sample holder, in accordance with an embodiment of the present invention.

An XPS system may be used to generate and to normalize an XPS signal. FIG. 3 is an illustration representing a system for obtaining and calibrating an XPS measurement and including a flux detector positioned at a sample holder, in accordance with an embodiment of the present invention.

Referring to FIG. 3, an XPS system 300 includes an XPS generation and detection system housed in a chamber 301 coupled with a computing system 318. The XPS generation and detection system includes an electron beam source 302 provided for generating an electron beam 304. Electron beam 304 is used to generate an X-ray beam 308 by bombarding an anode 306. A monochromator 309 is provided for generating a monochromatized X-ray beam 310 from X-ray beam 308. A sample holder 311 may be used to position a sample 399 in a pathway of monochromatized X-ray beam 310. A detector 314 is provided for collecting an XPS signal 312 generated by bombarding sample 399 with monochromatized X-ray beam 310. The XPS signal 312 is composed of photo-electrons. In accordance with an embodiment of the present invention, a flux detector 316 is provided for determining an estimated flux of monochromatized X-ray beam 310. In one embodiment, flux detector 316 is positioned at sample holder 316, as depicted in FIG. 3.

Flux detector 316 may be used to collect at least a portion of monochromatized X-ray beam 310 in order to determine an estimated flux of monochromatized X-ray beam 310. Thus, in one embodiment, an estimated flux of monochromatized X-ray beam 310 is determined directly by measuring the flux of monochromatized X-ray beam 310. However, by positioning flux detector 316 at the point where monochromatized X-ray beam 310 meets sample holder 311, as depicted in FIG. 3, flux detector 316 may not be able to collect a portion of monochromatized X-ray beam 310 at the same time that sample 399 is in place on sample holder 311. Thus, in an embodiment, when flux detector 316 is positioned at the point where monochromatized X-ray beam 310 meets sample holder 311, an estimated flux of monochromatized X-ray beam 310 needs to be determined when sample 399 is not present on sample holder 311. The flux is referred to as an 'estimated' flux, as opposed to a 'measured' flux which would be determined when a sample is actually present. In one embodiment, the estimated flux of the X-ray beam is obtained approximately immediately prior to generating the XPS signal from sample 399. In one embodiment, the estimated flux of the X-ray beam is obtained approximately immediately subsequent to generating the XPS signal from sample 399.

Computing system 318 includes a user interface 320 coupled with a computing portion 322 having a memory portion 324. Computing system 318 is provided for normalizing XPS signal 312 with the estimated flux of monochromatized X-ray beam 310. In accordance with an embodiment of the present invention, computing system 318 is for normalizing XPS signal 312 with an estimated flux of monochromatized X-ray beam 310 according to equation (1). In one embodiment, memory portion 324 has stored thereon a set of instructions for, when executed, using monochromatized X-ray beam 310 to generate XPS signal 312 from sample 399 and then normalizing XPS signal 312 with an estimated flux of monochromatized X-ray beam 310.

Figure 4:
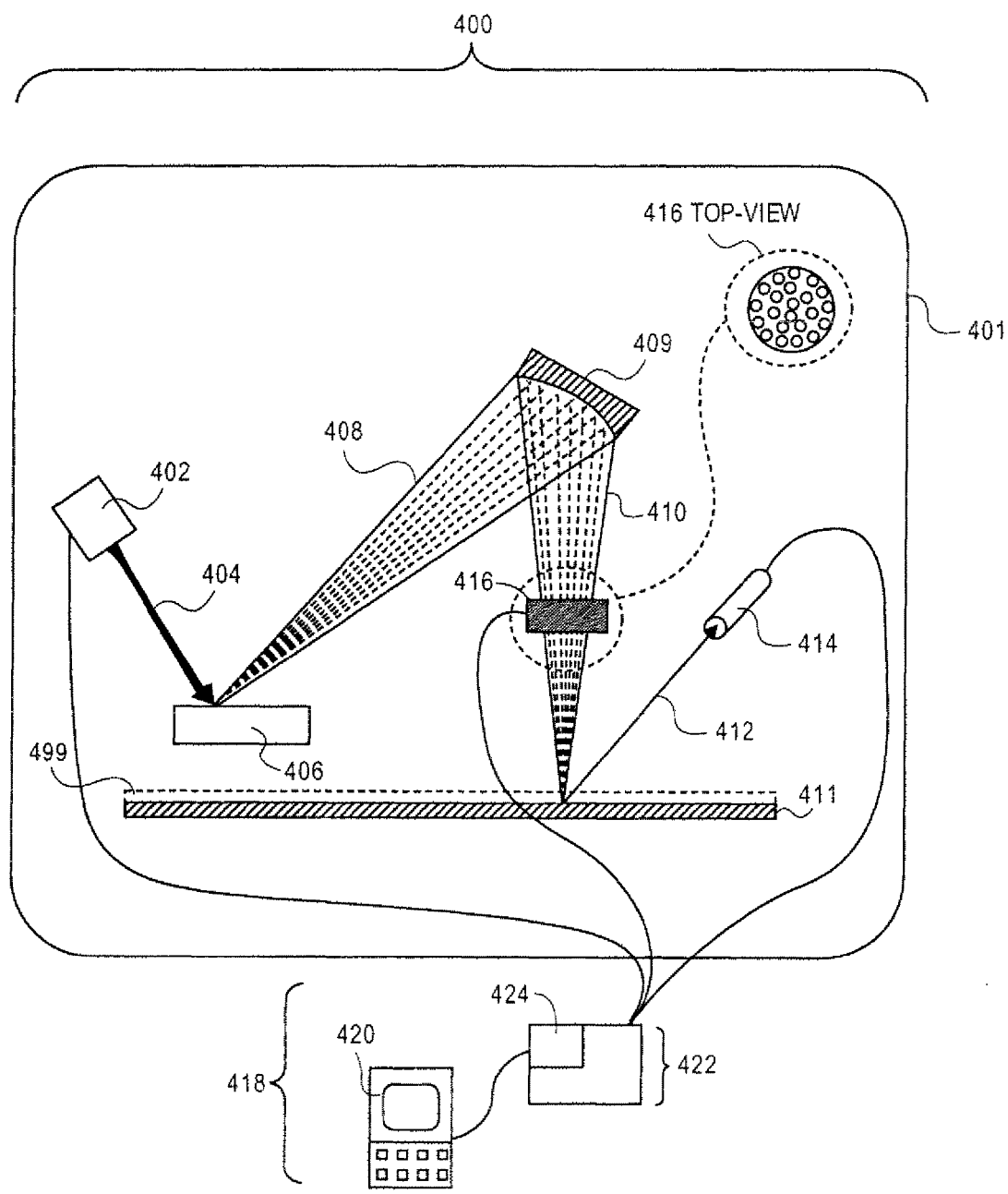
FIG. 4 is an illustration representing a system for obtaining and calibrating an X-ray photoelectron spectroscopy measurement and including a flux detector positioned along a pathway of a monochromatized X-ray beam, in accordance with an embodiment of the present invention.

In another aspect of the present invention, a flux detector need not be positioned at a sample holder. FIG. 4 is an illustration representing a system for obtaining and calibrating an XPS measurement and including a flux detector positioned along a pathway of a monochromatized X-ray beam, in accordance with an embodiment of the present invention.

Referring to FIG. 4, an XPS system 400 includes an XPS generation and detection system housed in a chamber 401 coupled with a computing system 418. The XPS generation and detection system includes an electron beam source 402, an anode 406, a monochromator 409, a sample holder 411 and a detector 414. In accordance with an embodiment of the present invention, a flux detector 416 is provided for determining a measured flux of monochromatized X-ray beam 410 in order to normalize XPS signal 412. In one embodiment, flux detector 416 is positioned along a pathway of monochromatized X-ray beam 410, between monochromator 409 and sample holder 411, as depicted in FIG. 4.

Flux detector 416 may be used to collect a portion of monochromatized X-ray beam 410 in order to determine a measured flux of monochromatized X-ray beam 410. Thus, in one embodiment, a measured flux of monochromatized X-ray beam 410 is determined directly by measuring the flux of monochromatized X-ray beam 410. By positioning flux detector 416 along a pathway between monochromator 409 and sample holder 411, a measured flux of monochromatized X-ray beam 410 may be collected while a sample 499 is bombarded to generate XPS signal 412. Hence, the flux so determined is referred to as a 'measured' flux. In accordance with an embodiment of the present invention, a measured flux of monochromatized X-ray beam 410 is determined at approximately the same time as XPS signal 412 is generated from sample 499. Thus, flux detector 416 may provide a closer to real-time determination of a measured flux versus, e.g., flux detector 316 described in association with FIG. 3. However, by collecting a portion of monochromatized X-ray beam 410 at the same time as bombarding sample 499 with monochromatized X-ray beam 410, the intensity of monochromatized X-ray beam 410 transmitted to sample 499 may be reduced. Accordingly, in an embodiment, as little of monochromatized X-ray beam 410 is collected by flux detector 416 as is possible to still accurately determine a measured flux of monochromatized X-ray beam 410. In one embodiment, flux detector 416 includes a very thin collection filter through which monochromatized X-ray beam 410 passes. In a specific embodiment, the collection filter is composed of aluminum and has a thickness approximately in the range of 0.5-1 microns. In one embodiment, flux detector 416 includes a collection filter having an array of holes to provide a physical transparency, as depicted by the "TOP-VIEW" of flux detector 416 in FIG. 4. In a specific embodiment, a collection filter of flux detector 416 has a physical transparency of approximately 90%.

A measured flux may be determined for the portion of monochromatized X-ray beam 410 that is removed by flux detector 416. In turn, this measured flux may be used to determine the flux for the portion of monochromatized X-ray beam 410 that is transmitted to sample holder 411, e.g., by multiplying the measured flux by a ratio of the portion that is transmitted over the portion that was removed. Thus, in accordance with an embodiment of the present invention, memory portion 424 of computing system 418 has stored thereon a set of instructions for, when executed, using monochromatized X-ray beam 410 to generate XPS signal 412 from sample 499 and then normalizing XPS signal 412 with a measured flux of monochromatized X-ray beam 410.

Figure 5:
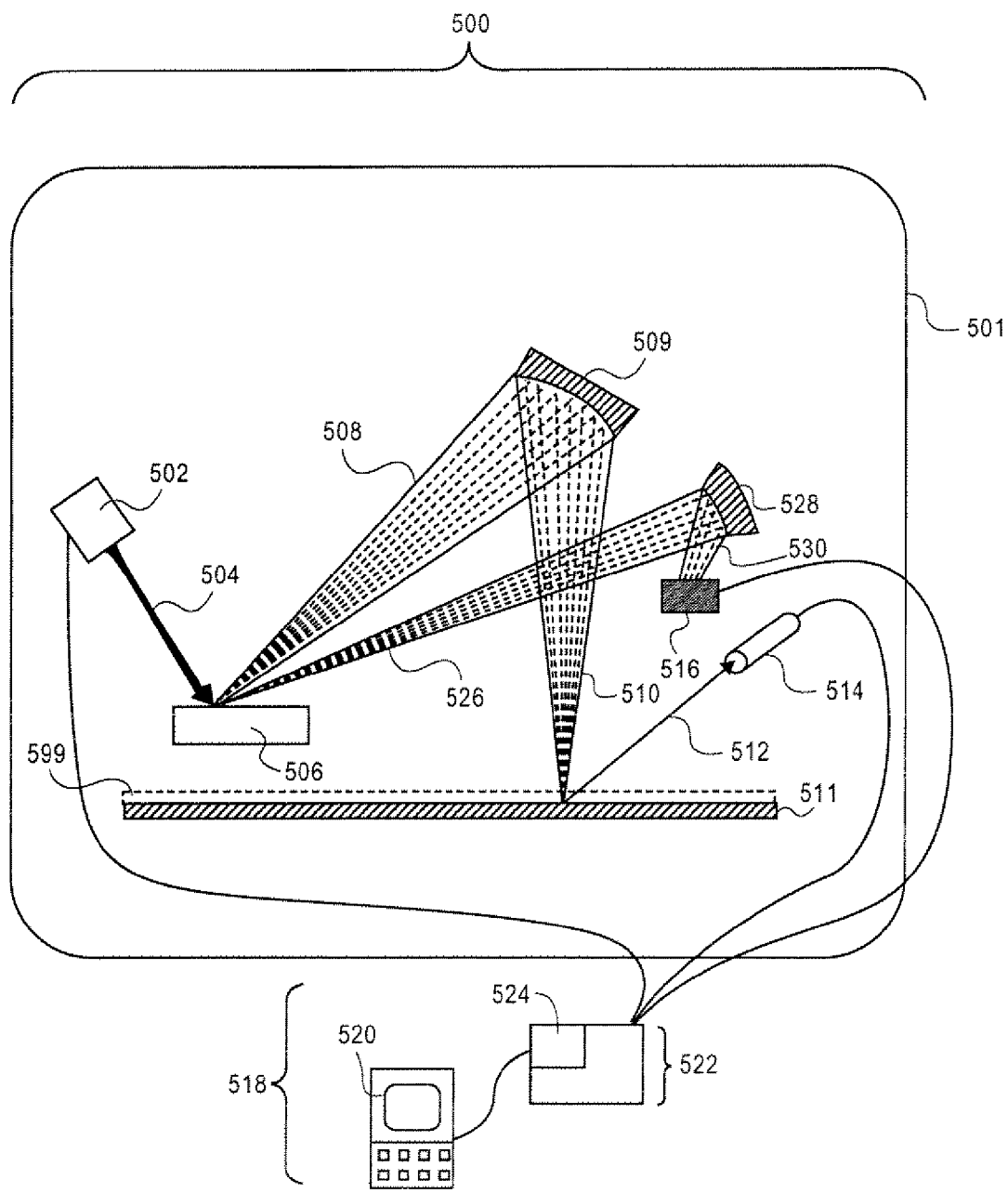
FIG. 5 is an illustration representing a system for obtaining and calibrating an X-ray photoelectron spectroscopy measurement and including a flux detector positioned to receive a secondary monochromatized X-ray beam, in accordance with an embodiment of the present invention.

In another aspect of the present invention, a flux detector need not be positioned along a pathway of a primary monochromatized X-ray beam. FIG. 5 is an illustration representing a system for obtaining and calibrating an XPS measurement and including a flux detector positioned to receive a secondary monochromatized X-ray beam, in accordance with an embodiment of the present invention.

Referring to FIG. 5, an XPS system 500 includes an XPS generation and detection system housed in a chamber 501 coupled with a computing system 518. The XPS generation and detection system includes an electron beam source 502, an anode 506, a monochromator 509, a sample holder 511 and a detector 514. In accordance with an embodiment of the present invention, a second monochromator 528 is provided for generating a second monochromatized X-ray beam 530 from a second X-ray beam 526. Second X-ray beam 526 may be generated at the same time as X-ray beam 508 when anode 506 is bombarded by electron beam 504 from electron beam source 502. In an embodiment, a flux detector 516 is provided for determining a measured flux of second monochromatized X-ray beam 530 in order to normalize XPS signal 512. In one embodiment, flux detector 516 is positioned to receive second monochromatized X-ray beam 530, as depicted in FIG. 5.

Flux detector 516 may be used to collect essentially all of second monochromatized X-ray beam 530 in order to determine a measured flux of second monochromatized X-ray beam 530. The measured flux of second monochromatized X-ray beam 530 may be used to determine a flux of monochromatized X-ray beam 510. Thus, in one embodiment, a flux of monochromatized X-ray beam 510 is determined indirectly by measuring the flux of second monochromatized X-ray beam 530. By using a measured flux of second monochromatized X-ray beam 530 to indirectly determine a flux of monochromatized X-ray beam 510, the flux of monochromatized X-ray beam 510 may be determined while a sample 599 is being bombarded to generate XPS signal 512. In accordance with an embodiment of the present invention, a flux of monochromatized X-ray beam 510 is determined by obtaining a measured flux of second monochromatized X-ray beam 530 at approximately the same time as generating XPS signal 512 from sample 599. Thus, flux detector 516 may provide a closer to real-time determination of a flux for monochromatized X-ray beam 510 versus, e.g., flux detector 316 described in association with FIG. 3. Additionally, in one embodiment, by keeping flux detector 516 out of a pathway of monochromatized X-ray beam 510, the intensity of monochromatized X-ray beam 510 that bombards sample 599 is maximized. However, by using a measured flux of second monochromatized X-ray beam 530 to determine a flux of monochromatized X-ray beam 510, care must be taken to ensure that the determination is a good fit. Accordingly, in an optimized embodiment, monochromators 509 and 528 have essentially the same features, such as material composition, size, and quality of surface smoothness. Such an embodiment, however, may not be practical for expense considerations and tool space constraints. Thus, in one embodiment, second monochromator 528 is of lower quality than monochromator 509. For example, in a particular embodiment, monochromator 509 is an ellipsoidal or spherical ultra-smooth mono-crystalline quartz monochromator and second monochromator 528 is a lower quality quartz crystal or a tungsten/silicon layered structure. Accordingly, second monochromatized X-ray beam 530 may be more diffuse at the point where it meets flux detector 516 than is monochromatized X-ray beam 510 at the point where it meets sample holder 511, as depicted in FIG. 5. In a specific embodiment, a flux determination using a measured flux of second monochromatized X-ray beam 530 to determine a flux of monochromatized X-ray beam 510 takes into consideration differences in diffuseness and signal intensity between the two monochromatized X-ray beams.

A measured flux determined for second monochromatized X-ray beam 530 may be used to determine a flux for monochromatized X-ray beam 510, e.g., by multiplying the measured flux by a ratio of the intensity of monochromatized X-ray beam 510 over the intensity of second monochromatized X-ray beam 530. In accordance with an embodiment of the present invention, memory portion 524 of computing system 518 has stored thereon a set of instructions for, when executed, using monochromatized X-ray beam 510 to generate XPS signal 512 from sample 599 and then normalizing XPS signal 512 with a flux of monochromatized X-ray beam 510, wherein the flux of monochromatized X-ray beam 510 is based on a measured flux determined for second monochromatized X-ray beam 530.

Figure 6:
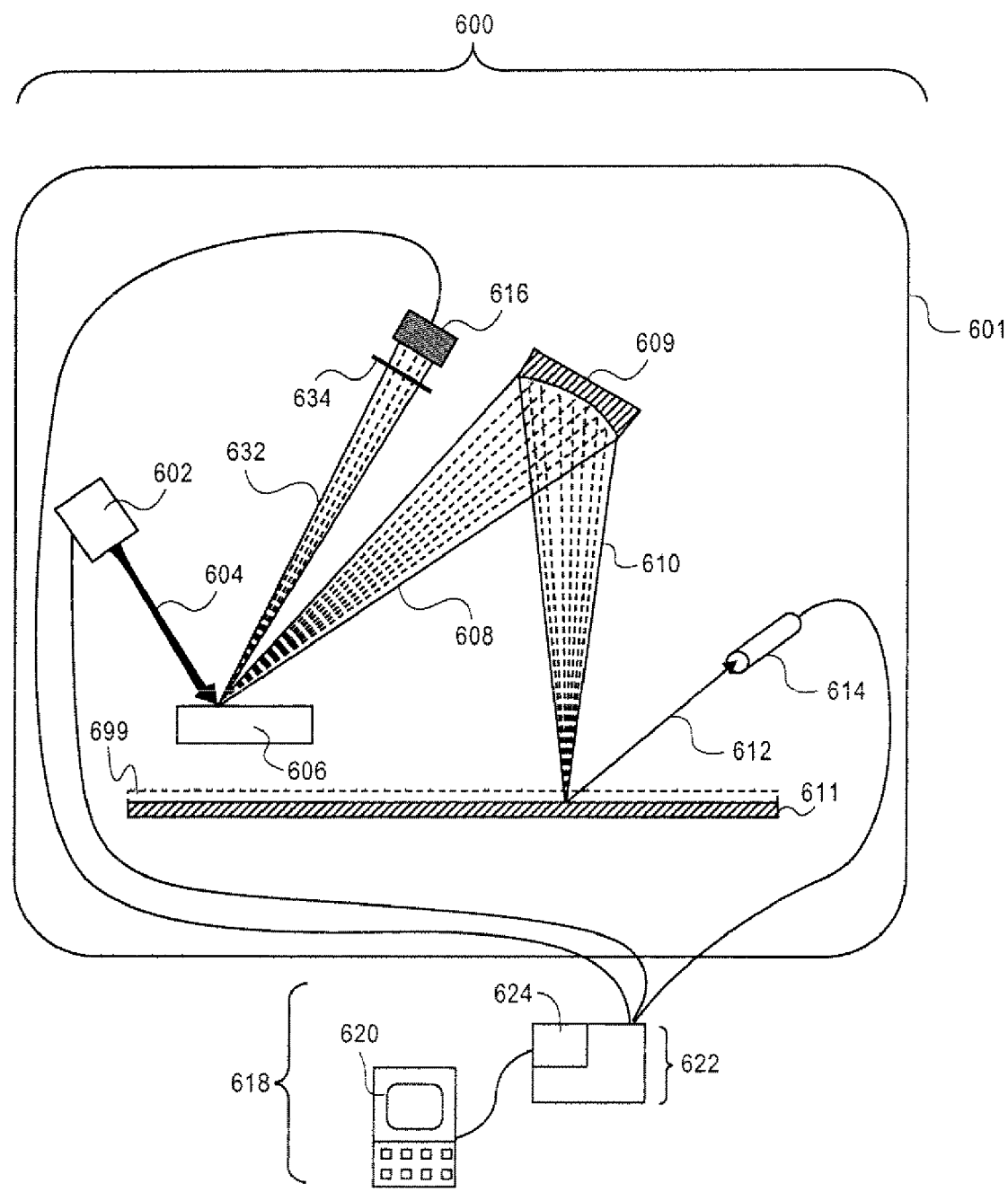
FIG. 6 is an illustration representing a system for obtaining and calibrating an X-ray photoelectron spectroscopy measurement and including a flux detector positioned to receive a secondary X-ray beam in accordance with an embodiment of the present invention.

In another aspect of the present invention, a flux detector need not be positioned along a pathway of a secondary monochromatized X-ray beam. FIG. 6 is an illustration representing a system for obtaining and calibrating an XPS measurement and including a flux detector positioned to receive a secondary X-ray beam, in accordance with an embodiment of the present invention.

Referring to FIG. 6, an XPS system 600 includes an XPS generation and detection system housed in a chamber 601 coupled with a computing system 618. The XPS generation and detection system includes an electron beam source 602, an anode 606, a monochromator 609, a sample holder 611 and a detector 614. In accordance with an embodiment of the present invention, a flux detector 616 is provided for determining a measured flux of a second X-ray beam 632 in order to normalize XPS signal 612. Second X-ray beam 632 may be generated at the same time as X-ray beam 608 when anode 606 is bombarded by electron beam 604 from electron beam source 602. In one embodiment, flux detector 616 is positioned to receive second X-ray beam 632, as depicted in FIG. 6.

Flux detector 616 may be used to collect essentially all of second X-ray beam 632 in order to determine a measured flux of second X-ray beam 632. The measured flux of second X-ray beam 632 may be used to determine a flux of monochromatized X-ray beam 610. Thus, in one embodiment, a flux of monochromatized X-ray beam 610 is determined indirectly by measuring the flux of second X-ray beam 632. By using a measured flux of second X-ray beam 632 to indirectly determine a flux of monochromatized X-ray beam 610, the flux of monochromatized X-ray beam 610 may be determined while a sample 699 is bombarded to generate XPS signal 612. In accordance with an embodiment of the present invention, a flux of monochromatized X-ray beam 610 is determined by obtaining a measured flux of second X-ray beam 632 at approximately the same time as generating XPS signal 612 from sample 699. Thus, flux detector 616 may provide a closer to real-time determination of an estimated flux versus, e.g., flux detector 316 described in association with FIG. 3. Additionally, in one embodiment, by keeping flux detector 616 out of a pathway of monochromatized X-ray beam 610, the intensity of monochromatized X-ray beam 610 that bombards sample 699 is maximized. However, the measured flux of second X-ray beam 632 represents a flux that has not been monochromatized by a monochromator. Thus, when using a measured flux of second X-ray beam 632 to determine a flux of monochromatized X-ray beam 610, care must be taken to ensure that the determination is a good fit. Accordingly, in an embodiment, monochromatization may be approximated by using a filter 634 in between anode 606 and flux detector 616, as depicted in FIG. 6. In one embodiment, the filter is composed of aluminum and has a thickness approximately in the range of 10-20 microns, permitting essentially only AlK$\alpha$ X-rays to be transmitted to flux detector 616. In a specific embodiment, a flux determination using a measured flux of second X-ray beam 632 to determine an estimated flux of monochromatized X-ray beam 610 takes into consideration differences in signal intensity and composition between the two X-ray beams.

A measured flux determined for the filtered portion of second X-ray beam 632 may be used to determine a flux for monochromatized X-ray beam 610, e.g., by multiplying the measured flux by a ratio of the intensity of monochromatized X-ray beam 610 over the intensity of the filtered portion of second X-ray beam 632. In accordance with an embodiment of the present invention, memory portion 624 of computing system 618 has stored thereon a set of instructions for, when executed, using monochromatized X-ray beam 610 to generate XPS signal 612 from sample 699 and then normalizing XPS signal 612 with a flux of monochromatized X-ray beam 610, wherein the flux of monochromatized X-ray beam 610 is based on a measured flux determined for a filtered portion of second X-ray beam 632.

Figure 7:
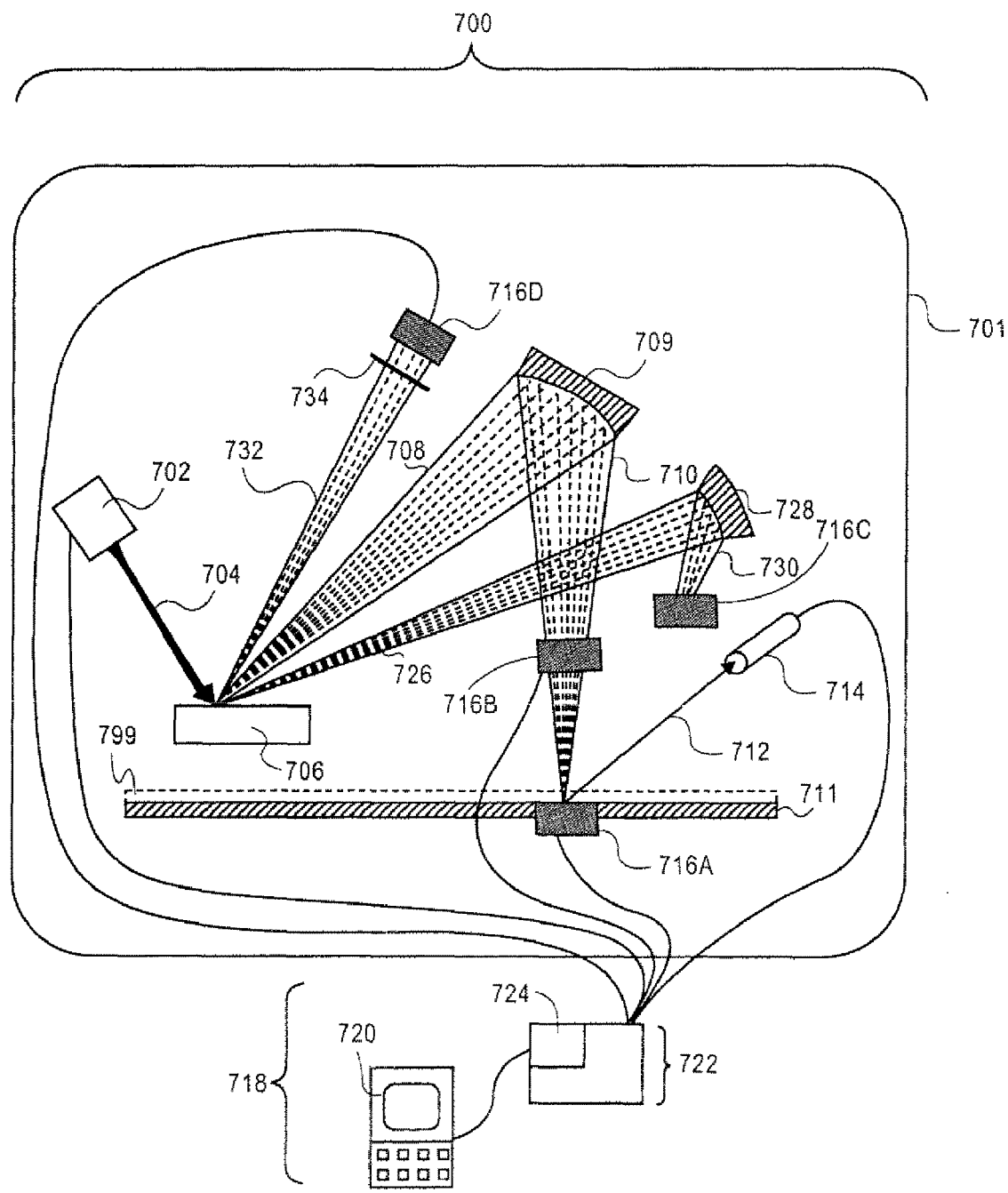
FIG. 7 is an illustration representing a system for obtaining and calibrating an X-ray photoelectron spectroscopy measurement and including multiple flux detectors, in accordance with an embodiment of the present invention.

In order to fully exploit flux detectors for normalizing XPS signals, a system may include more than one flux detector. FIG. 7 is an illustration representing a system for obtaining and calibrating an XPS measurement and including multiple flux detectors, in accordance with an embodiment of the present invention.

The positioning of flux detectors 316, 416, 516 and 616, described in association with FIGS. 3-6 respectively, enables optimization of certain attributes of flux detection for XPS signal calibration, but each may also have an associated drawback. For example, flux detector 316 enables direct measurement of the flux of the same monochromatized X-ray beam used to bombard a sample without impacting the intensity of the portion of the monochromatized X-ray beam. However, flux detector 316 may not be useable for flux detection at the same time that a sample is in place on a sample holder, Flux detector 416 enables direct measurement of the flux of the same monochromatized X-ray beam used to bombard a sample at the same time that a sample is in place on a sample holder. However, flux detector 416 may reduce the intensity of the portion of the monochromatized X-ray beam transmitted to bombard the sample. Flux detector 516 may enable flux detection at the same time that a sample is in place on a sample holder without reducing the intensity of the monochromatized X-ray beam used to bombard the sample. However, because flux detector 516 is used to determine a measured flux of a second monochromatized X-ray beam, only an indirect determination may be made for the flux of the monochromatized X-ray beam that is actually used to bombard a sample. Finally, flux detector 616 may also enable flux detection at the same time that a sample is in place on a sample holder without reducing the intensity of the monochromatized X-ray beam used to bombard the sample. However, because flux detector 516 is used to determine a measured flux of a second X-ray beam, like flux detector 516, only an indirect determination may be made for the flux of the monochromatized X-ray beam that is actually used to bombard a sample. Accordingly, for optimal flux determination, it may be desirable to use two or more flux detectors in concert with one another.

Referring to FIG. 7, an XPS system 700 includes an XPS generation and detection system housed in a chamber 701 coupled with a computing system 718. The XPS generation and detection system includes an electron beam source 702 provided for generating an electron beam 704. Electron beam 704 is used to generate an X-ray beam 708 by bombarding an anode 706. A monochromator 709 is provided for generating a monochromatized X-ray beam 710 from X-ray beam 708. A sample holder 711 may be used to position a sample 799 in a pathway of monochromatized X-ray beam 710. A detector 714 is provided for collecting an XPS signal 712 generated by bombarding sample 799 with monochromatized X-ray beam 710. In accordance with an embodiment of the present invention, two or more flux detectors, e.g. two or more of 716A, 716B, 716C or 7166D, are provided for determining a measured or estimated flux of monochromatized X-ray beam 710. In one embodiment, flux detector 716A is positioned at sample holder 711, flux detector 716B is positioned along a pathway of monochromatized X-ray beam 710, flux detector 716C is positioned to receive a second monochromatized X-ray beam 730 generated from a second X-ray beam 726, and flux detector 716D is positioned to receive a third X-ray beam 732, all of which are depicted in FIG. 7.

Two or more flux detectors, e.g. two or more of flux detectors 716A, 716B, 716C or 7166D, may be incorporated into an XPS system in order to take advantage of various attributes of the positioning selections available for the flux detectors. For example, in accordance with an embodiment of the present invention, an XPS system includes flux detectors 716A and 716C. Flux detector 716A enables direct measurement of the flux of the same monochromatized X-ray beam used to bombard sample 799. However, flux detector 716A may not be useable for flux detection at the same time that sample 799 is in place on sample holder 711. On the other hand, Flux detector 716C enables flux detection at the same time that sample 799 is in place on sample holder 711. However, because flux detector 716C is used to determine a measured flux of a second monochromatized X-ray beam, only an indirect determination may be made for the flux of monochromatized X-ray beam 710. When used in concert, flux detector 716C may be implemented to verify that the flux of X-ray beams generated from anode 706 remained approximately constant prior to the introduction of sample 799, when sample 799 is present, and subsequent to the removal of sample 799. Accordingly, in one embodiment, flux detector 716C is used to verify that the estimated flux of monochromatized X-ray beam 710, as detected by flux detector 716A prior to and subsequent to the bombarding of sample 799, is a reasonable estimate of the flux of monochromatized X-ray beam 710 during the time sample 799 is actually bombarded. By way of example, in a specific embodiment, a change in flux of a monochromatized X-ray beam during bombarding of sample 799 would otherwise go undetected by flux detector 716A, but would be detected by flux detector 716C. However, the estimated flux of the monochromatized X-ray beam determined by flux detector 716A can be adjusted by a corrective flux from flux detector 716C to compensate for any change determined by flux detector 716C. In that embodiment, the adjusted estimated flux of monochromatized X-ray beam 710 is then used to normalize XPS signal 712.

In another example, and in accordance with another embodiment of the present invention, an XPS system includes flux detectors 716A and 716D. Flux detector 716A enables direct measurement of the flux of the same monochromatized X-ray beam used to bombard sample 799. However, flux detector 716A may not be useable for flux detection at the same time that sample 799 is in place on sample holder 711. On the other hand, Flux detector 716D enables flux detection at the same time that sample 799 is in place on sample holder 711. However, because flux detector 716D is used to determine a measured flux of a second X-ray beam, only an indirect determination may be made for the flux of monochromatized X-ray beam 710. Like flux detector 716C, when used in concert with flux detector 716A, flux detector 716D may be implemented to verify that the flux of X-ray beams generated from anode 706 remained approximately constant prior to the introduction of sample 799, when sample 799 is present, and subsequent to the removal of sample 799. Accordingly, in one embodiment, flux detector 716D is used to verify that the estimated flux of monochromatized X-ray beam 710, as detected by flux detector 716A prior to and subsequent to the bombarding of sample 799, is a reasonable estimate of the flux of monochromatized X-ray beam 710 during the time sample 799 is actually bombarded. By way of example, in a specific embodiment, a change in flux of a monochromatized X-ray beam during bombarding of sample 799 would otherwise go undetected by flux detector 716A, but would be detected by flux detector 716D. However, the estimated flux of the monochromatized X-ray beam determined by flux detector 716A can be adjusted by a corrective flux from flux detector 716D to compensate for any change determined by flux detector 716D. In that embodiment, the adjusted estimated flux of monochromatized X-ray beam 710 is then used to normalize XPS signal 712.

Computing system 718 includes a user interface 720 coupled with a computing portion 722 having a memory portion 724. Computing system 718 is provided for normalizing XPS signal 712 with the measured or estimated flux of monochromatized X-ray beam 710. In accordance with an embodiment of the present invention, computing system 718 is for normalizing XPS signal 712 with a measured or estimated flux of monochromatized X-ray beam 710 according to equation (1). In one embodiment, memory portion 724 has stored thereon a set of instructions for, when executed, using monochromatized X-ray beam 710 to generate XPS signal 712 from sample 799 and then normalizing XPS signal 712 with a measured or estimated flux of monochromatized X-ray beam 710, wherein the measured or estimated flux is determined by two or more flux detectors working in concert. Although the above two examples combine flux detector 716A with either flux detector 716C or 716D, the present invention is not limited to those combinations. In accordance with an embodiment of the present invention, an XPS system includes two or more flux detectors and at least two of the flux detectors work together in concert to provide a measured or estimated flux for an X-ray beam used to bombard sample 799 and generate XPS signal 712. In one embodiment, the two or more flux detectors are positioned at positions such as, but not limited to, the positions of flux detectors 716A, 716B, 716C or 716D.

In an aspect of the invention, an XPS measurement may be made upon introduction of a sample into an XPS system, such as but not limited to XPS systems 300, 400, 500, 600 and 700. In accordance with an embodiment of the present invention, the sample is bombarded with an X-ray beam. In response to bombardment by the X-ray beam, and XPS signal (composed of photo-electrons) may be emitted from the sample and collected in a detector. In an embodiment, the XPS signal is correlated with the atomic dose of a particular atomic species in the sample. In one embodiment, the atomic dose is correlated with a sample property such as, but not limited to, the thickness of a film in the sample, the depth to which the particular atomic species is incorporated into the sample or a concentration ratio of several atomic species in the sample. For example, in a particular embodiment, an XPS signal for a dielectric layer such as, but not limited to, silicon dioxide, silicon oxy-nitride, aluminum oxide or hafnium oxide, is obtained. In accordance with an embodiment of the present invention, the XPS signal is correlated to a property of the dielectric film without having to obtain, reference or ratio an XPS signal of, e.g., an underlying substrate or reference film. In one embodiment, the XPS signal is normalized with a determined flux of the X-ray beam used to generate the XPS signal.

Thus, a method and a system for calibrating an XPS measurement are described. In accordance with an embodiment of the present invention, the method includes using an X-ray beam to generate an XPS signal from a sample. The XPS signal is normalized with a measured or estimated flux of the X-ray beam. In accordance with another embodiment of the present invention, the system includes an X-ray source for generating an X-ray beam and a sample holder for positioning a sample in a pathway of the X-ray beam. A detector is included for collecting an XPS signal generated by bombarding the sample with the X-ray beam. A flux detector is included for determining a measured or estimated flux of the X-ray beam. A computing system is included for normalizing the XPS signal with the measured or estimated flux of the X-ray beam.

What is claimed is:

1. A method for calibrating an X-ray photoelectron spectroscopy (XPS) measurement, comprising:
   using an X-ray beam to generate an XPS signal from a sample; and
   normalizing said XPS signal with a flux of said X-ray beam according to the following equation: $XPS_{calibrated} = XPS_{measured} \times (Flux_{calibrated}/Flux_{measured\ or\ estimated})$.

2. The method of claim 1, wherein said flux of said X-ray beam is obtained prior to generating said XPS signal from said sample.

3. The method of claim 1, wherein said flux of said X-ray beam is obtained subsequent to generating said XPS signal from said sample.

4. The method of claim 1, wherein said flux of said X-ray beam is obtained at approximately the same time as generating said XPS signal from said sample.

5. A method for calibrating an X-ray photoelectron spectroscopy (XPS) measurement, comprising:
   generating an X-ray beam from an anode;
   generating a monochromatized X-ray beam from said X-ray beam;
   bombarding a sample with said monochromatized X-ray beam;
   generating an XPS signal from said sample; and
   normalizing said XPS signal with a flux of said monochromatized X-ray beam according to the following equation: $XPS_{calibrated} = XPS_{measured} \times (Flux_{calibrated}/Flux_{measured\ or\ estimated})$.

6. The method of claim 5, wherein said flux of said monochromatized X-ray beam is obtained prior to bombarding said sample with said monochromatized X-ray beam.

7. The method of claim 5, wherein said flux of said monochromatized X-ray beam is obtained subsequent to bombarding said sample with said monochromatized X-ray beam.

8. The method of claim 5, wherein said flux of said monochromatized X-ray beam is obtained at approximately the same time as bombarding said sample with said monochromatized X-ray beam.

9. The method of claim 5, wherein said flux of said monochromatized X-ray beam is determined directly by measuring the flux of said monochromatized X-ray beam.

10. The method of claim 5, wherein said flux of said monochromatized X-ray beam is determined indirectly by measuring the flux of a second monochromatized X-ray beam generated from a second X-ray beam, wherein said second X-ray beam is generated from said anode.

11. The method of claim 5, wherein said flux of said monochromatized X-ray beam is determined indirectly by measuring the flux of a second X-ray beam generated from said anode.

12. A system for calibrating an X-ray photoelectron spectroscopy (XPS) measurement, comprising:
   an X-ray source for generating an X-ray beam;
   a sample holder for positioning a sample in a pathway of said X-ray beam;
   a detector for collecting an XPS signal generated by bombarding said sample with said X-ray beam;
   a flux detector for determining a flux of said X-ray beam; and
   a computing system configured to normalize said XPS signal with said flux of said X-ray beam according to the following equation: $XPS_{calibrated} = XPS_{measured} \times (Flux_{calibrated}/Flux_{measured\ or\ estimated})$.

13. The system of claim 12, wherein said flux detector is positioned at said sample holder.

14. The system of claim 12, wherein said flux detector is positioned along said pathway between said X-ray source and said sample holder.

15. A system for calibrating an X-ray photoelectron spectroscopy (XPS) measurement, comprising:
an electron beam source for generating an electron beam;
an anode for generating an X-ray beam when said anode is bombarded by said electron beam;
a monochromator for generating a monochromatized X-ray beam from said X-ray beam;
a sample holder for positioning a sample in a pathway of said monochromatized X-ray beam;
a detector for collecting an XPS signal generated by bombarding said sample with said monochromatized X-ray beam;
a flux detector for determining a flux of said monochromatized X-ray beam; and
a computing system configured to normalize said XPS signal with said flux of said monochromatized X-ray beam according to the following equation: $XPS_{calibrated} = XPS_{measured} \times (Flux_{calibrated}/Flux_{measured\ or\ estimated})$.

16. The system of claim 15, wherein said flux detector is positioned at said sample holder.

17. The system of claim 16, wherein said flux of said monochromatized X-ray beam is determined directly.

18. The system of claim 15, wherein said flux detector is positioned along said pathway between said monochromator and said sample holder.

19. The system of claim 18, wherein said flux of said monochromatized X-ray beam is determined directly.

20. The system of claim 15, wherein said anode is also for generating a second X-ray beam when said anode is bombarded by said electron beam, the system further comprising:
a second monochromator for generating a second monochromatized X-ray beam from said second X-ray beam, wherein said flux detector is positioned to receive said second monochromatized X-ray beam.

21. The system of claim 20, wherein said flux of said monochromatized X-ray beam is determined indirectly by measuring a flux of said second monochromatized X-ray beam.

22. The system of claim 15, wherein said anode is also for generating a second X-ray beam when said anode is bombarded by said electron beam, and wherein said flux detector is positioned to receive said second X-ray beam.

23. The system of claim 22, wherein said flux of said monochromatized X-ray beam is determined indirectly by measuring a flux of said second X-ray beam.

24. The system of claim 15, wherein said flux detector is positioned at said sample holder, the system further comprising:
a second flux detector for determining a corrective flux of said monochromatized X-ray beam.

25. The system of claim 24, wherein said anode is also for generating a second X-ray beam when said anode is bombarded by said electron beam, the system further comprising:
a second monochromator for generating a second monochromatized X-ray beam from said second X-ray beam, wherein said second flux detector is positioned to receive said second monochromatized X-ray beam.

26. The system of claim 24, wherein said anode is also for generating a second X-ray beam when said anode is bombarded by said electron beam, and wherein said second flux detector is positioned to receive said second X-ray beam.

* * * * *